United States Patent [19]
Cooper

[11] Patent Number: 5,669,887
[45] Date of Patent: Sep. 23, 1997

[54] RETRACTABLE NON-REUSABLE NEEDLE

[76] Inventor: William L. Cooper, 1722 Union Ave., Niceville, Fla. 32578

[21] Appl. No.: 635,659

[22] Filed: Apr. 22, 1996

[51] Int. Cl.$^6$ .................................................. A61M 5/32
[52] U.S. Cl. ................................... 604/195; 604/248
[58] Field of Search ................................ 604/110, 195, 604/198, 263, 246, 248, 192, 187, 218, 220

[56] References Cited

U.S. PATENT DOCUMENTS

| | | | |
|---|---|---|---|
| 4,187,849 | 2/1980 | Stim | 64/248 X |
| 5,108,378 | 4/1992 | Firth et al. | 604/192 |
| 5,188,601 | 2/1993 | King | 604/110 |
| 5,211,628 | 5/1993 | Marshall | 604/110 |
| 5,215,533 | 6/1993 | Robb | 604/195 |
| 5,222,944 | 6/1993 | Harris | 604/110 |
| 5,232,458 | 8/1993 | Chen | 604/195 |
| 5,242,400 | 9/1993 | Blake, III et al. | 604/110 |
| 5,242,402 | 9/1993 | Chen | 604/110 |
| 5,279,581 | 1/1994 | Firth et al. | 604/198 |
| 5,290,255 | 3/1994 | Vallelunga et al. | 604/110 X |
| 5,308,329 | 5/1994 | Mazur et al. | 604/195 X |
| 5,330,440 | 7/1994 | Stanners et al. | 604/195 |
| 5,346,474 | 9/1994 | King | 604/110 |
| 5,374,250 | 12/1994 | Dixon | 604/198 X |

*Primary Examiner*—John D. Yasko
*Attorney, Agent, or Firm*—Peter Loffler

[57] ABSTRACT

A retractable needle assembly is disclosed. The needle assembly consists of a syringe body, having a needle assembly on one end and a plunger assembly on the opposing end. The needle assembly, which enables and disables fluid communication between the needle and fluid reservoir, comprises a generally cylindrical body sealably disposed within the lower interior of the syringe body. The cylindrical body is rotatable, facilitated by a knurled ring, within the syringe body. Rotation of the cylindrical body causes either enablement or disablement of the needle assembly. Tabs, located on the syringe body are received within notches, separated by one-way and two-way ramps, located on the cylindrical body, such that the ramps facilitate either temporary or permanent disablement of the device. Plunger lock means are also disclosed.

20 Claims, 12 Drawing Sheets

RETRACTABLE NON-REUSABLE NEEDLE

BACKGROUND OF THE INVENTION

1. Field of the Invention

The present invention relates to a retractable needle, and in more particular, to a retractable needle that uses rotating knob-operated cooperating disc stacks and hydrostatic pressure from the needle's fluid reservoir to permanently withdraw the needle.

2. Background of the Prior Art

Needles are a routine part of any medical setting. It is standard medical practice to use a needle once and then discard it. Such practice prevents the spread of disease. However, with the recent spread of diseases such as HIV and Hepatitis, not only is the use-once-and-discard procedure mandatory, the spread has called for further precautions.

When a needle is used, the needle's end has the patient's blood and other bodily fluids on it. If another person, such as a health care worker, comes in contact with this end, and thereby contracts the disease, the experience may prove fatal. Therefore, it has become necessary to shield people from a used needle's contaminated end.

Many examples of non-reusable shielded needles are found in the prior art. Examples of such devices include U.S. Pat. No. 5,242,402 and U.S. Pat. No. 5,232,458 issued to Chen, U.S. Pat. No. 5,242,400 issued to Blake III et al., U.S. Pat. No. 5,222,944 issued to Harris, U.S. Pat. No. 5,279,581 and U.S. Pat. No. 5,108,378 issued to Firth et al., U.S. Pat. No. 5,215,533 issued to Robb, U.S. Pat. No. 5,211,628 issued to Marshall, U.S. Pat. No. 5,188,601 issued to King, and many others.

There are two main approaches to shielding the needle tip in order to prevent accidental pricks. The first method involves a sheath, encompassing the needle body, being slid into place over the needle after use. The other approach involves retraction of the needle into the needle body after use. Some retraction methods permanently lock the needle into its retracted mode. As an additional safety measure, many devices have a break-off plunger to further eliminate the potential for reuse or reloading of the needle.

While the devices presently found in the art work with differing levels of success, they suffer from complexity over a standard needle. Such complexity renders the needle expensive to manufacture to the point of being cost-prohibitive to purchase. In a setting having high needle use, substantial additional expense may be the critical factor in deciding to use a regular non-shielded needle. Furthermore, the complexity increases the potential for failure of the needle shielding means.

A needle is needed that will shield the needle tip after use and will permanently render the needle non-reusable. Such a needle must be relatively simple and inexpensive to manufacture and must have a very low potential for failure.

SUMMARY OF THE INVENTION

The device of the present invention meets the above mentioned need in the art. The present invention comprises a syringe assembly that can be permanently disabled and thereafter the needle can be safely and permanently withdrawn into the interior of the syringe body, preventing accidental pricking from a used needle.

The device comprises a syringe body having plunger slidably disposed within one end and a needle assembly rotatably disposed within the other. Rotation of the needle assembly will selectively enable and disable fluid flow between the needle and the syringe's fluid reservoir.

The needle assembly comprises a cylindrical body having a top, middle and bottom section with a needle attached to the bottom section. A fluid passage, having a top portion laterally offset from the central axis of the cylindrical body, and a bottom portion, extends through the cylindrical body placing the needle in fluid connection with the reservoir. One or more slotted portions extends through the middle section. One or more sealing discs are disposed within each of the slotted portions. A pair of generally semi-circular plates wrap around the middle section and receive the ends of the sealing discs. One or two protrusion slots, located between the plates, receive one or two rectangular protrusions located on the inside of the syringe body and hold the plates rotatably fixed. Rotation of the cylindrical body causes an aperture on the seal disc to either align or mis-align the top portion of the fluid passage with the bottom portion of the fluid passage for enabling fluid connection between reservoir and needle or disabling fluid connection respectively.

One or two slotted portions are located on the bottom section and align with the respective rectangular protrusions only when the user places the device into a permanently disabled state. By being so aligned, the cylindrical body may be retracted into the interior of the syringe body.

Alternatively, one of the plates has a fluid passage located therein. Rotation of the cylindrical body causes this fluid passage to align or mis-align with the top portion and the bottom portion.

Alternatively, the cylindrical body may have a slotted portion having a round section, a vertical section, and a horizontal section integrally disposed therebetween. A tumbler having an aperture and an extension passing through the cylindrical body and received within a diagonal slot located on one of the plates. Rotation of the cylindrical body causes the aperture to either align or mis-align with the top portion of the fluid passage (in this case located on the central axis of the cylindrical body) and the bottom portion of the fluid passage.

In each case, rotation of the cylindrical body is accomplished by the use of an open-ended knurled ring having a base with a non-symmetric aperture located thereon. The aperture engages a protrusion, in corresponding shape to the knurled ring aperture, located on the base of the bottom section. One or more windows located on the knurled ring correspond with one or more color bands located on the syringe body for determining the state of enablement of the device.

One or more tabs are located on the inner circumference of the syringe body. Each tab is received in one of four notches located on the outer circumference of the bottom section. The notch within which each tab is located determines device state. One and two way ramps either permit or prohibit return to a prior state.

For added security, the plunger can be permanently locked in place when the plunger is fully retracted.

BRIEF DESCRIPTION OF THE DRAWINGS

Similar reference numerals refer to similar parts through out the several views of the drawings.

DETAILED DESCRIPTION OF THE PREFERRED EMBODIMENT

The present invention is comprised of a plunger 10, a syringe body 12, a retractable, sealable needle assembly 14, and a rotatable knurled ring 16. The syringe body 12 is hollow. The open ends of the syringe body 12 are located at the top or plunger end 18 and at the bottom or needle assembly end 20 and a fluid reservoir 22 therebetween.

Slidably disposed within the top end 18 of the syringe body 12 is the plunger 10 comprised of, from top to bottom, a handle 24, a shaft 26, and a base 28. The handle 24 may be open 30 and nominally flat or it may be close-looped 32 to facilitate single-finger aspiration. Encompassing the outer perimeter of the base 28 is an O-ring or other suitable sealing means 34 for preventing fluid flow between the outer perimeter of the base 28 and the inner perimeter of the syringe body 12. The base 28 is solid to prevent fluid flow therefrom.

Extending outwardly from the top edge of the exterior syringe body 12 surface is a finger grip flange 36. The flange 36 extends sufficiently far from the exterior syringe body 12 surface to prevent fingers from sliding over it while gripping the syringe body 12.

Located along the inner perimeter of the bottom edge of the syringe body 12, in proximity to the needle end 20, are one or more spaced apart cantilever tabs 38 having tab protrusions 40. One or more vertically disposed spaced apart rectangular protrusion 42 are disposed within the hollow inner region of the syringe body 12.

Located on the outside of the syringe body 12 adjacent to the bottom edge of the syringe body 12 are one or more spaced apart multi-colored strips 44. The colored strips 44 have a green portion 46, a first yellow portion 48, a second yellow portion 50 (in a different shade from the shade of the first yellow portion 48), and a red portion 52.

Encompassing the outer perimeter of the syringe body 12, above the color strips 44, is a projecting ring 54. The top side 56 of the projecting ring 54 projects squarely from the syringe body 12. The bottom side 58 of the projecting ring 54 is ramped. Located above the projecting ring 54 on the outer perimeter of the syringe body 12 are one or more spaced apart series of fluid graduation marks 60 for gauging the quantity of fluid in the inner hollow region of the syringe body 12.

Disposed principally within the bottom of the inner hollow region of the syringe body 12 is the retractable, lockable, and sealable needle assembly 14 having a top 64, cylindrical middle section 66, and bottom 68. The top 64 of the needle assembly body 14 is flat or shaped in similar fashion to the relief of the bottom end of the plunger base 28. The bottom 66 of the needle assembly 14 has a non-symmetric geometric protrusion 70. Extending from either the geometric protrusion 70 or directly from the bottom of the needle assembly 14 is either a needle 72 or a threaded needle base 74 bearing a needle 72. The sides of the needle assembly 14 follow the cylindrical shape of the hollow inner region of the syringe body 12.

The needle assembly 14 has a top flange 76, and a bottom flange 78. The axis of symmetry of the cylindrical middle section 66 extends from top 64 to bottom 68 and lies at the center of the cylindrical syringe body 12. Encompassing the outer perimeter of the top flange 78 is an O-ring or other suitable sealing means 80 for preventing fluid from flowing between the needle assembly 14 and the inner perimeter of the syringe body 12. The bottom flange 78 and the seal-wrapped top flange 76 fit snugly within the inner surface of the inner hollow region of the syringe body 12. On the surface of the cylindrical middle section 66 of the needle assembly body 14 are a plurality of round protrusions 82.

Located on the bottom flange 78 are one or more ramp assemblies 84, one ramp assembly 84 for each of the cantilever tabs 38. Each ramp assembly 84 comprises a first one-way ramp 86, a two-way ramp 88, and a second one-way ramp 90. The tab protrusions 40 at the free ends of the cantilever tabs 38 extend into, and can slide along, the ramp assemblies 84. Also located on the bottom flange 78 are one or more flange slots 92 that extend from top to bottom, one flange slot 92 for each of the rectangular protrusion 42 extending from the inner syringe body surface. The flange slots 92 are cut into the bottom flange 78 to the depth of the cylindrical middle section 66 of the needle assembly 14.

A horizontally disposed slot 94 passes through the center of the cylindrical middle section 66 of the needle assembly 14. A sealing disc 96, having an aperture 98, is disposed in the horizontal slot 94, fitting snugly within the top and bottom of the horizontal slot 94. A fluid passage 100, which is a hollow portion, extends from the top of the needle assembly 14 to the needle 72 or the bottom center of the threaded needle base 74. The fluid passage 100 extends from top to bottom through the needle assembly 14 and the aperture 98 of the sealing disc 96. The bottom portion 102 of the fluid passage 100 extending from the bottom of the horizontal slot 94 may be centered on the needle 72 or threaded needle base 74 while the top portion 102 of the fluid passage 100 extending from the top of the needle assembly 14 to the horizontal slot 94 may be laterally offset from the bottom portion 102 of the fluid passage 100. The aperture 98 in the sealing disc 96 fluid connects the top portion 104 and bottom portion 102. Rotating the needle assembly 14 about the sealing disc 96 in the horizontal slot 94 can mis-align the slot aperture 98 and disconnect the top portion 104 and the bottom portion 102. The snug fit between the sealing disc 96 and the top and bottom surfaces of the horizontal slot 94 prevents fluid from flowing between the sealing disc 96 and the top and bottom surfaces of the horizontal slot 94. Tabs 106 on the sealing disc 96 extend from one or both ends of the horizontal slot 94 such that the ends of the sealing disc tabs 106 are even with the outer edges of the top flange 76 and the bottom flange 78.

One or more generally semi-circular plates 108 are placed around the cylindrical middle section 66 of the needle assembly 14 between the bottom of the top flange 76 and the top of the bottom flange 78. The generally semi-circular plates 108 extend from one flange slot 92 to the next flange slot 92 (if more than one slot is present). The generally semi-circular plates 108 have sufficient circumference to span the unslotted lengths of the bottom flange 78. The generally semi-circular plates 108 have rounded depressions 110 along their inner surfaces.

Disc tab holes 112 penetrate the generally semi-circular plates 108 from the inside to the outside. The sealing disc tabs 106 are received into the disc tab holes 112. The fluid passage 100 extending through the horizontal slot 94 in the needle assembly 14 is connected or disconnected by rotating the needle assembly 14 within the semi-circular plates 108 and around the sealing disc 96.

The needle assembly 14 is assembled by placing the sealing disc 96 into the horizontal slot 94 and placing the generally semi-circular plates 108 around the exterior of the cylindrical middle section 66. The sealing disc tabs 106 fit into the semi-circular plates' disc tab holes 112. The gaps between the semi-circular plates are aligned with the flange slots 92. The multiple rounded protrusions 82 on the surface of the cylindrical middle section 66 of the needle assembly 14 are received into the rounded depressions 110 to keep the semi-circular plates 108 aligned during assembly. The device of the present invention is assembled by slidably inserting the needle assembly 14 needle end down into the top of the syringe body 12. The needle assembly 14 slides into the syringe body so the rectangular protrusions 42 on the inner surface of the syringe body 12 slide into the flange slots 92 and the gaps between the semi-circular plates 108. The bottom of the top flange 76 rests against the top of the rectangular protrusions 42. The cantilever tabs 38 and ramp assemblies 84 are located such that the tab protrusions 40 on the free ends of the cantilever tabs 38 slide into notches at the non-ramped sides of the second one-way ramps 90. The sealing disc 96 in this configuration does not fluid connect the top portion 104 and the bottom portion 102. The rectangular protrusions 42 on the inner surface of the syringe body 12 extend down to the top of the bottom flange 78 when the needle assembly 14 is fully inserted into the syringe body 12.

The free ends of the cantilever tabs 38 are now lifted and the needle assembly 14 is rotated until the cantilever tabs 38 are positioned in the notches at the non-ramped side of the first one-way ramps 86. Now the sealing disc 96 fluid connects the top portion 104 and the bottom portion 102. Fluid is free to move through the continuous fluid passage 100 and the plunger 10 may be fully inserted. Rotating the needle assembly 14 has mis-aligned the flange slots 92 and the rectangular protrusions 42 on the inner surface of the syringe body 12. The needle assembly 14 can not be slidably moved along the hollow inner region of the syringe body 12 in this configuration. The free ends of the cantilever tabs 38 are now lifted and the needle assembly 14 is rotated until the cantilever tabs 38 are positioned in the notches at the ramped side of the first one-way ramps 86. Now the sealing disc 96 does not connect the top portion 104 and the bottom portion 102. The flange slots 92 and the rectangular protrusions 42 on the inner surface of the syringe body 12 are still mis-aligned. The needle assembly 14 can not be slidably moved along the hollow inner region of the syringe body 12 in this configuration.

A knurled ring 114 comprises an open-ended tube 116, having a knurled outer circumference 118, and a plate 120 attached to its bottom. A flange 122 extends outwardly from the exterior knurled ring surface as a finger guard to prevent fingers from sliding over the bottom end of the syringe body 12 and contacting the needle 72. The middle of the plate 122 contains an aperture 124 in corresponding shape to the shape of the relief of the non-symmetric protrusion 70 on the bottom of the needle assembly 14. The top edge of the knurled ring 114 is multiply split from the top of the ring to the middle portion of the ring into numerous cantilever ring tabs 126.

Assembly of the device is completed by sliding the knurled ring 114 upwards over the needle 72 or threaded needle base 74 so that the aperture 124 in the knurled ring plate 122 aligns with the non-symmetric protrusion 70 on the bottom of the needle assembly 14. The cantilever ring tabs 126 have small protrusions 128 along the inside of their top edges. These protrusions 128 slide up the sloped bottom surface of the projecting ring 54 on the syringe body 12 exterior surface and snap over the non-sloped upper surface of the projecting ring 54 to hold the knurled ring 114 in place. The knurled ring 114 cannot be removed without damage to and probable disablement of the device. The knurled ring 114 engages the needle assembly 14 via the non-symmetrical protrusion 70 so that rotating the knurled ring 114 causes corresponding rotation of the needle assembly 14. The generally semi-circular plates 108 are fixed in place by the rectangular protrusions 42 on the syringe body 12 inner surface. The sealing disc 96 remains motionless as it is connected to the generally semi-circular plates 108. Rotating the knurled ring 114 and the needle assembly 14 about the sealing disc allows the top portion 104 and bottom portion 102 to be connected and disconnected.

The knurled ring 114 has a smooth surface at several windows 129 along is periphery. A single portion of each multi-colored strip 44 is viewable through each of the windows 129.

The complete syringe assembly is now ready for use. The complete assembly has four operating configurations, each denoted by a different color showing through the knurled ring windows 129. Initially, windows 129 with the green colored strips 46 showing through the windows 129. The green strips 46 denotes that the syringe has not been used. In this configuration the top portion 104 and the bottom portion 102 are disconnected by the sealing disc 96. The flange slots 92 are mis-aligned with the rectangular protrusions 42 so the needle assembly can not be slidably moved. Hydrostatic pressure in the fluid reservoir 22 (hollow inner region of the syringe body 12 between the top of the needle assembly 14 and the bottom of the plunger base 28) does not allow the plunger 10 to be slidably moved. Rotating the knurled ring 114 causes the cantilever tabs 38 to ride over the first one-way ramp 86 and the windows 129 show the first yellow portions 48. The knurled ring 114 can not be turned back to the initial green portion state without harming the device. In the first yellow portion state the needle assembly 14 has been rotated about the sealing disc 96 so the top portion 104 is now fluid connected with the bottom portion 102. Fluid can pass from the needle 72 or threaded needle base 74 to the fluid reservoir or vice versa. The flange slots 92 remain mis-aligned with the rectangular protrusions 42 so the needle assembly can not be slidably moved.

If the knurled ring 114 is rotated further until the windows 129 are positioned over the second yellow portions 50, the needle assembly 14 will again rotate, with the cantilever tabs 38 passing over the two-way ramp. This causes the sealing disc to fluid disconnect the top portion 104 and the bottom portion 102. The flange slots 92 remain mis-aligned with the rectangular protrusions 42 so the needle assembly can not be slidably moved. Hydrostatic pressure again does not allow the plunger 10 to be slidably moved. The syringe is now disabled, but can be re-enabled as the knurled ring can be counter-rotated back to the first yellow portion position. The two-way ramp 88 assure this maneuver.

This functionality is especially useful when the fluid introduced into the fluid reservoir in the syringe body 12 is a medicine such as a vaccine. The knurled ring 114 can be temporarily rotated to disable the device, and the health professional can re-enable the device when the patient is present.

When the syringe is used and is to be discarded, the knurled ring 114 is rotated so the windows 129 are positioned over the red color portions 52. This causes the cantilever tabs 38 to pass over the second one-way ramp 90. The knurled ring can no longer be rotated in either direction. In this configuration the top portion 104 and the bottom portion 102 are fluid disconnected by the sealing disc 96. The flange slots 92, however, are aligned with the rectangular protrusions 42 so the needle assembly can be slidably moved upwardly. Hydrostatic pressure in the fluid reservoir allows the plunger 10 and the needle assembly 14 to be slidably moved.

Pulling on the plunger 10 generates a hydrostatic pressure in the fluid reservoir. This hydrostatic pressure transfers part of the pulling (or pushing) force to the needle assembly 14, causing it to move with the plunger movement. Contact between the top flange 76 and the rectangular protrusions 42 prevents the needle assembly 14 from being pushed out the bottom end of the syringe body 12. The needle 72 or threaded needle base 74 is shielded from incidental contact by being withdrawn into the syringe body 12. The aperture 124 in the knurled ring's base plate 124 is small enough to prevent finger insertion into the syringe body 12. The suitable sealing means on the plunger base 28 and top flange 76 prevent fluid leakage from the fluid reservoir 22 as the reservoir 22 moves in the syringe body 12.

Figure 1:
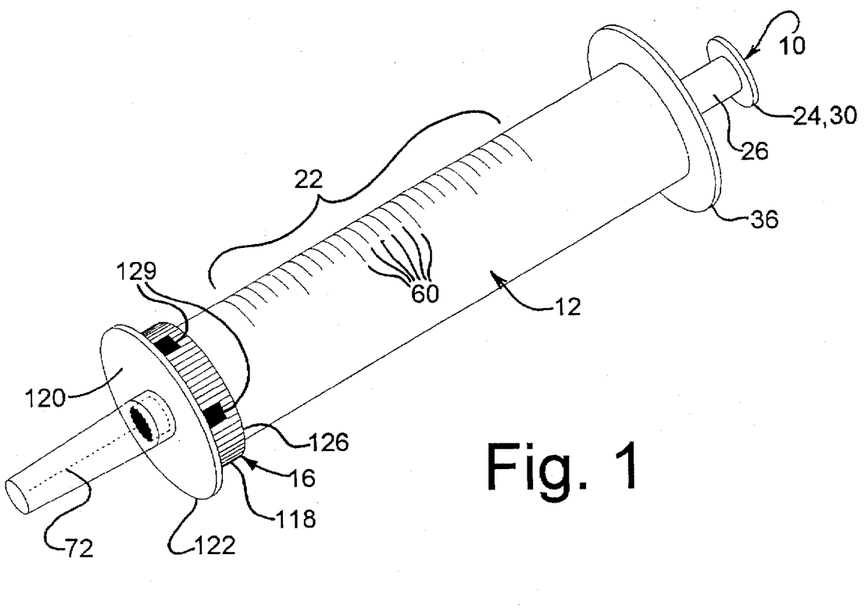
FIG. 1 is an isometric of the syringe assembly device of the present invention.
Figure 2:
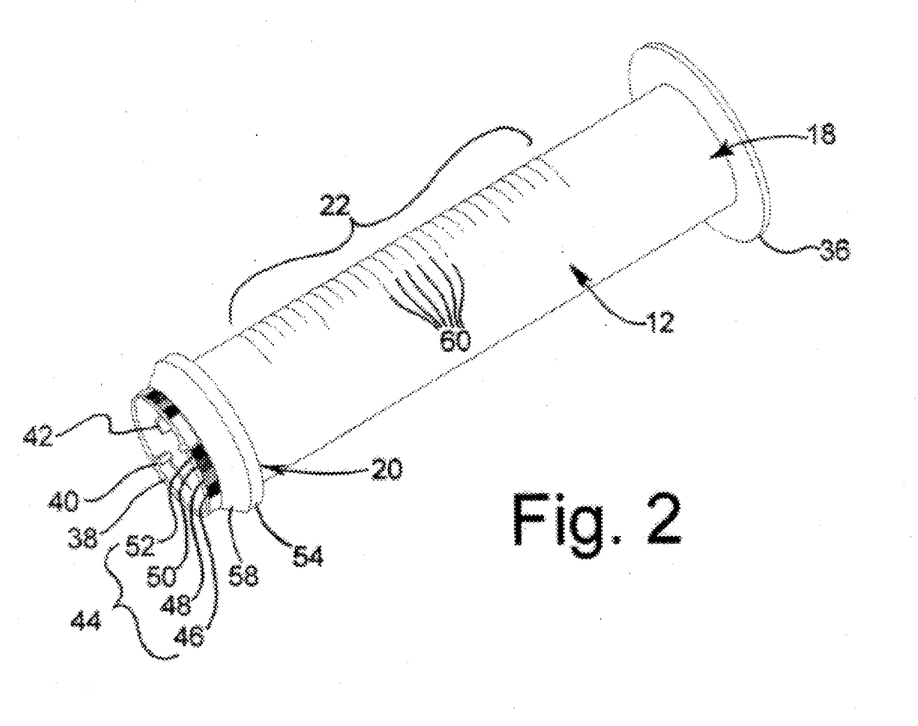
FIG. 2 is an isometric view of syringe body.
Figure 3:
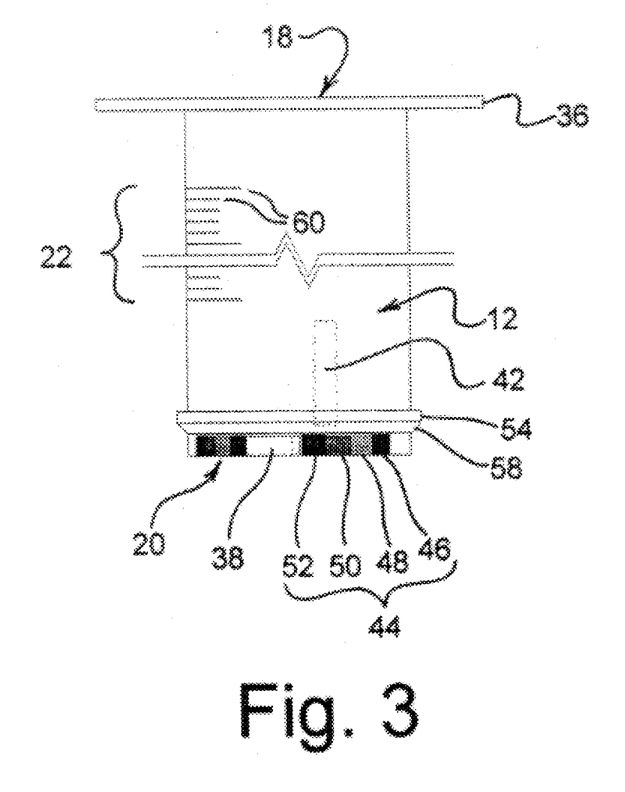
FIG. 3 is a side view of the syringe body.
Figure 4A:
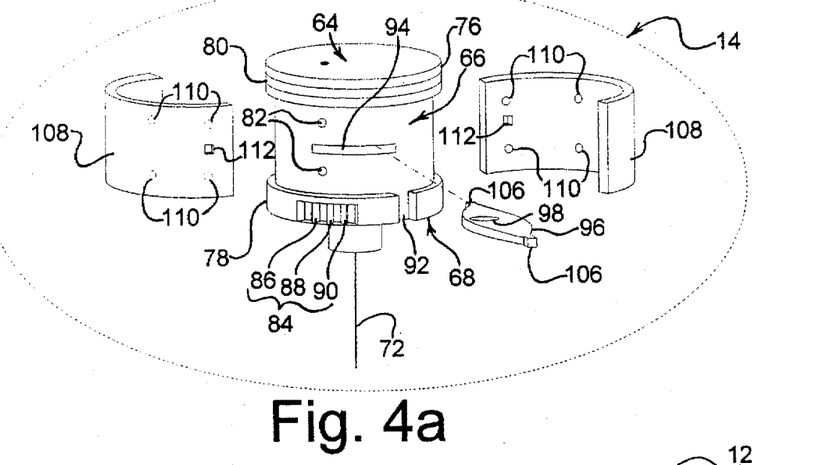
FIG. 4a is an isometric view of the single disc needle assembly.
Figure 4B:
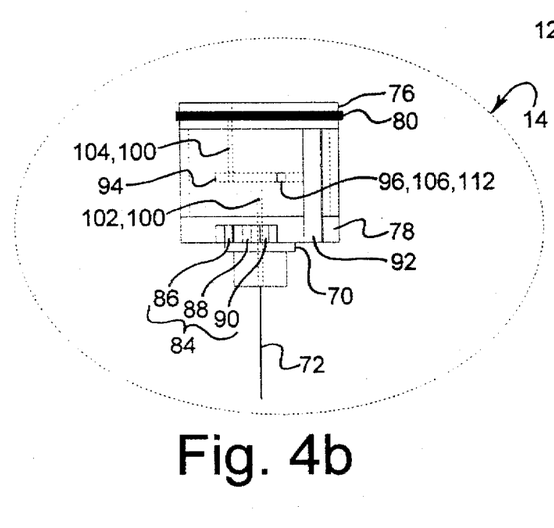
FIG. 4b is a side view of the single disc needle assembly.
Figure 4C:
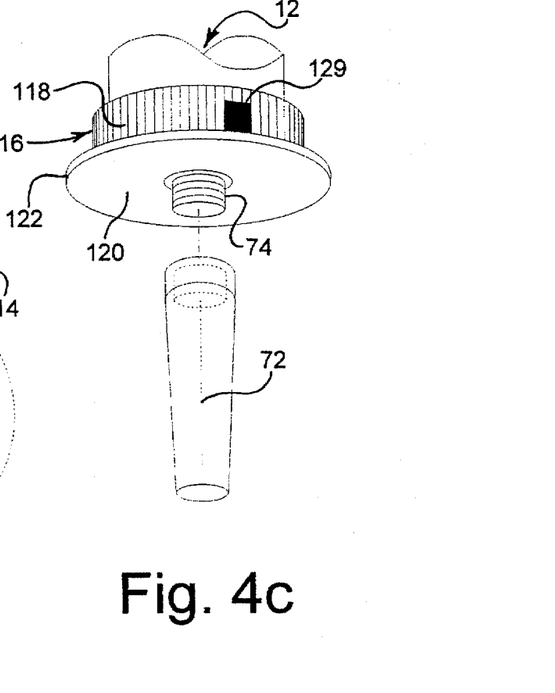
FIG. 4c is an isometric view of the needle attached prior to use.
Figure 5A:
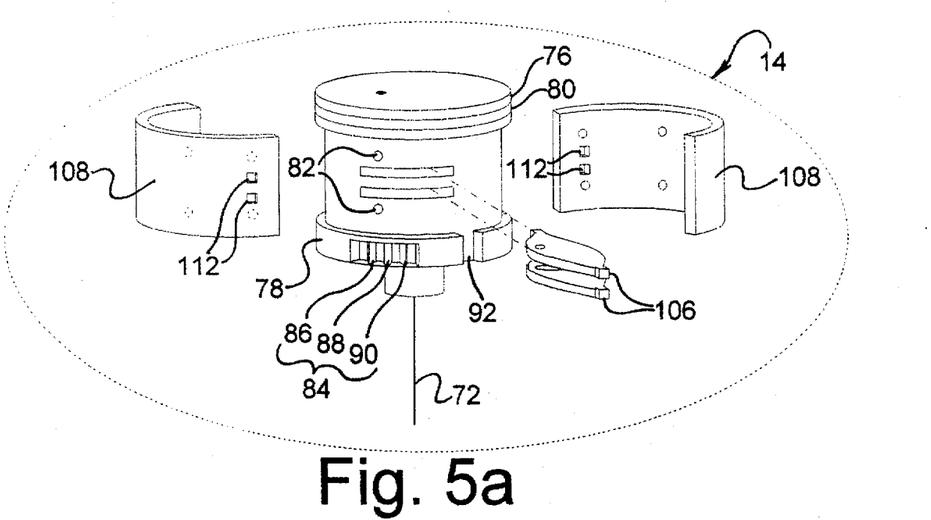
FIG. 5a is an isometric view of the multiple disc needle assembly.
Figure 5B:
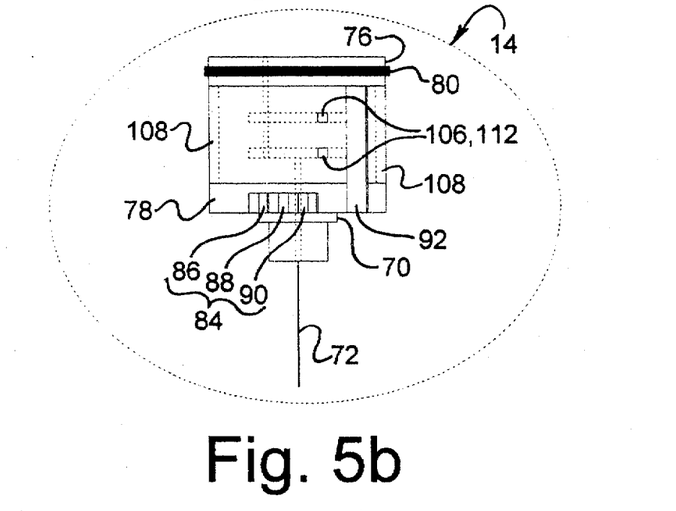
FIG. 5b is a side view of the multiple disc needle assembly.
Figure 6A:
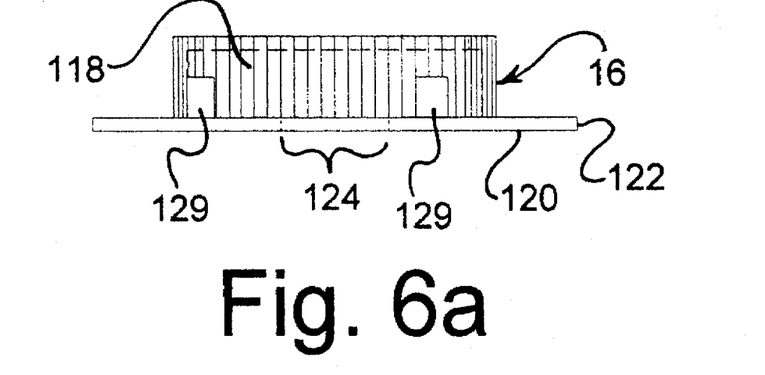
FIG. 6a is a side view of the knurled ring.
Figure 6B:
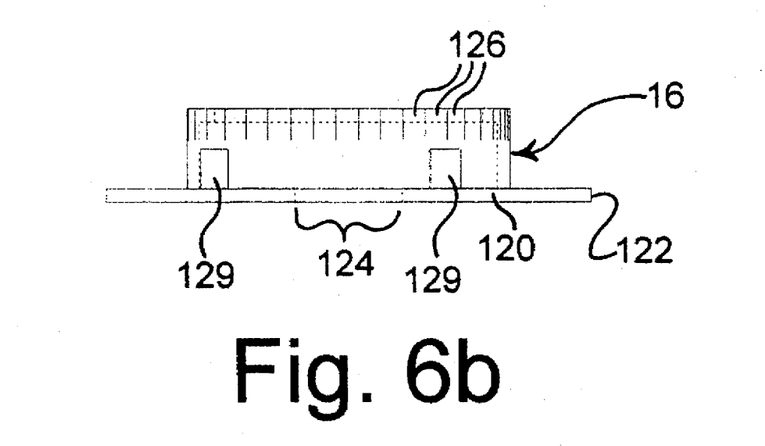
FIG. 6b is a side view of the knurled ring without the knurled surface.
Figure 6C:
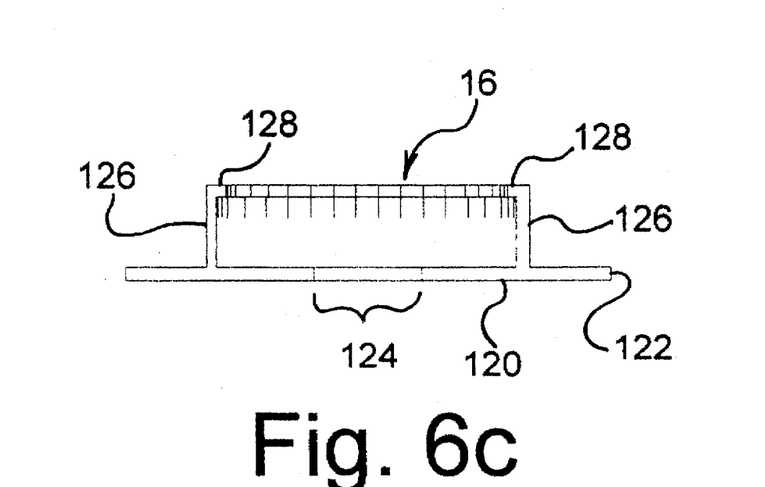
FIG. 6c is a cutaway view of the knurled ring.

As seen in FIGS. 5a and 5b, multiple sealing discs 96, each having an aperture can disposed within multiple horizontal slots 94 can be utilized. Each sealing disc 96 has a sealing disc tab 106 on either end with each sealing disc tab 106 received within a respective disc tab hole 112 located on the generally semi-circular disc plates 108. In all other respects, the multiple sealing disc tab assembly would function in identical fashion to the single sealing disc 96 configuration.

Figure 7A:
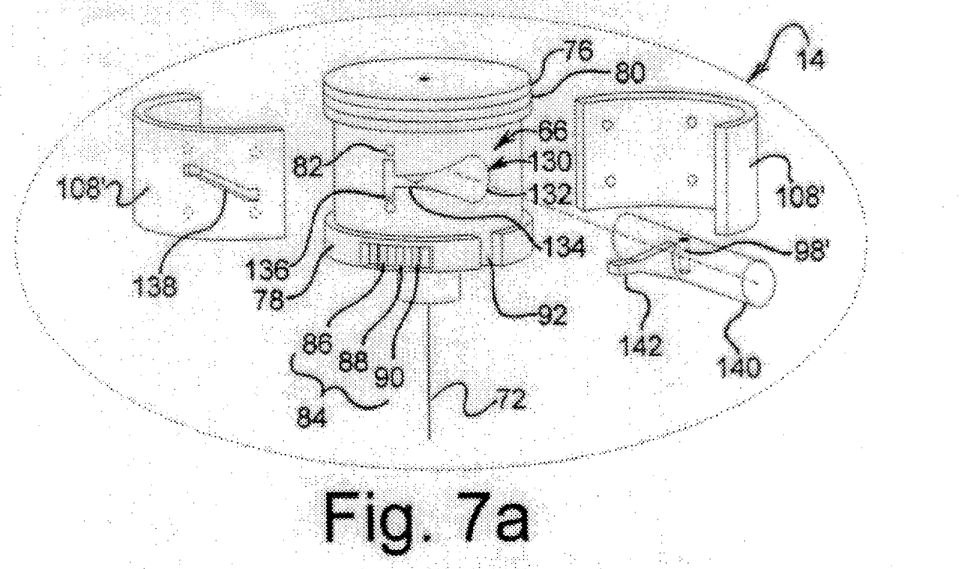
FIG. 7a is an isometric view of the tumbler needle assembly.
Figure 7B:
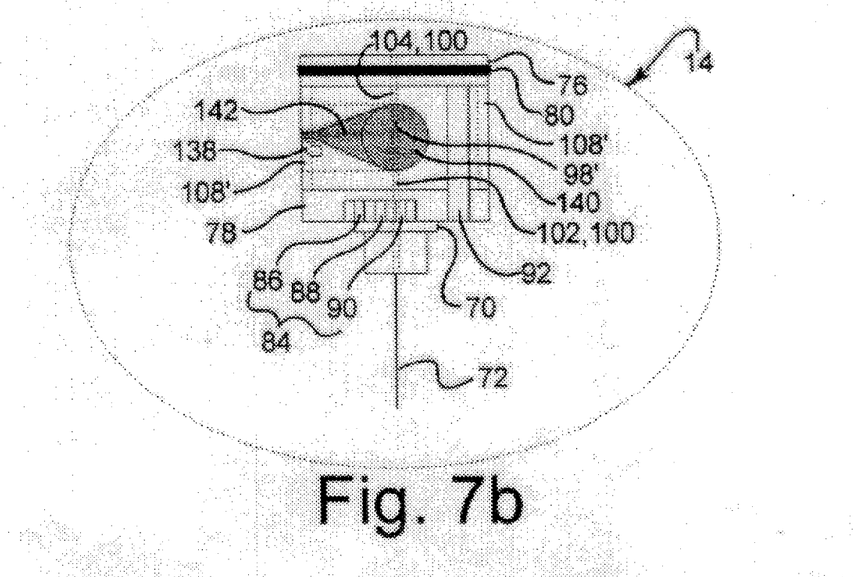
FIG. 7b is a side view of the tumbler needle assembly.

As seen in FIGS. 7a and 7b, in an alternate embodiment of the needle assembly 14 the cylindrical middle section 66 has a slotted portion 130 having a rounded section 132, a horizontal section 134, and a vertical section 136. One of the generally semi-circular plates 108' has a diagonally disposed slotted portion 138. A cylindrical rotating tumbler 140, having an extension 142 and an aperture 98' passing through the tumbler 140, is disposed within the rounded section 132 of the slotted portion 130. The extension 142 passes through the vertical section 136 and through the diagonally disposed slotted portion 138.

When the device is initially assembled (view window 128 over the green portion 46), the extension 142 is located at the top of the diagonally disposed slotted portion 138. In this position, the aperture 98' is mis-aligned with the top portion 104 and the bottom portion 102 thereby fluid disconnecting the two portions. When the knurled ring 114 is rotated (view window over first yellow portion 48), the cylindrical body rotates thereby causing the extension 142, to travel partially down the diagonally disposed slotted portion 138. This causes the tumbler 140 to rotate and to align with the aperture with the top portion 104 and the bottom portion 102 thereby fluid connecting the two portions. When the knurled ring 114 is further rotated (view window 128 over the second yellow portion 50), the needle assembly 14 further rotates thereby causing the extension 142, to travel further down the diagonally disposed slotted portion 138. This causes the tumbler 140 to rotate and to once again mis-align the aperture with the top portion 104 and the bottom portion 102 once again fluid disconnecting the two portions. Further rotation of the knurled ring 114 (view window over red portion 52) will continue the mis-alignment of the aperture with the top portion 104 and the bottom portion 102.

Figure 8:
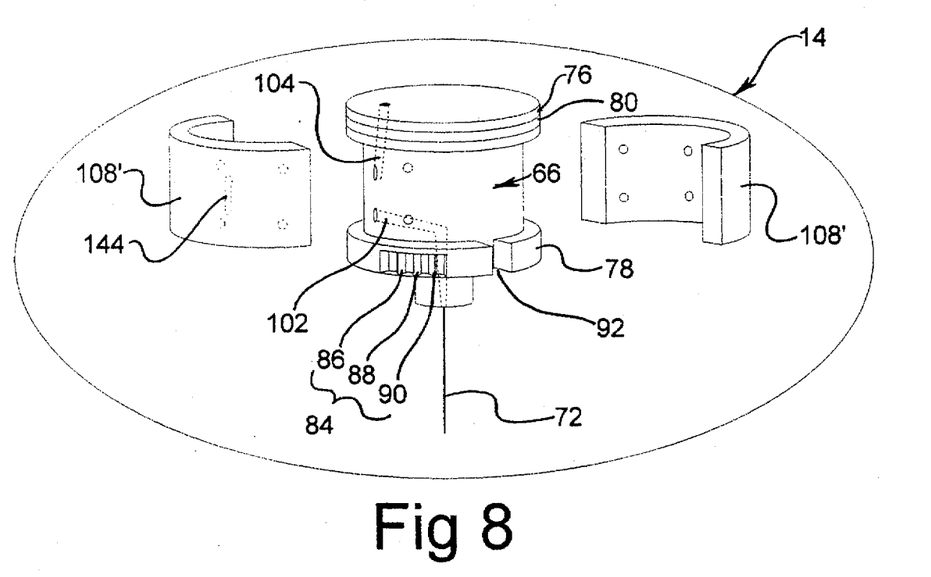
FIG. 8 is an isometric view of the external fluid passage needle assembly.
Figures 9A, 9B:
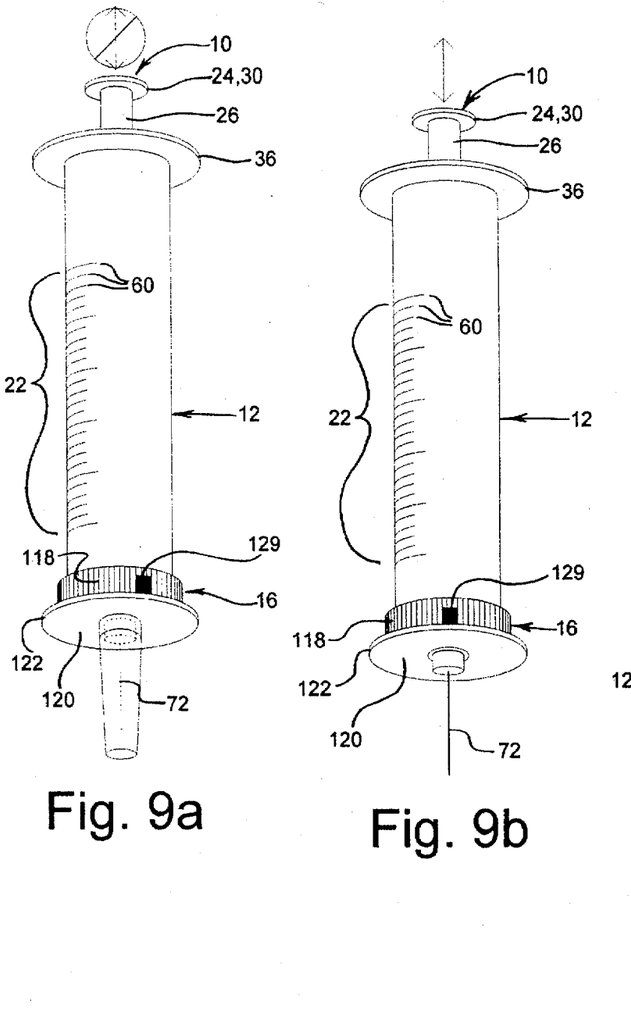
FIG. 9a is an isometric view of the syringe assembly in a new state.
FIG. 9b is an isometric view of the syringe assembly in use.
Figure 9C:
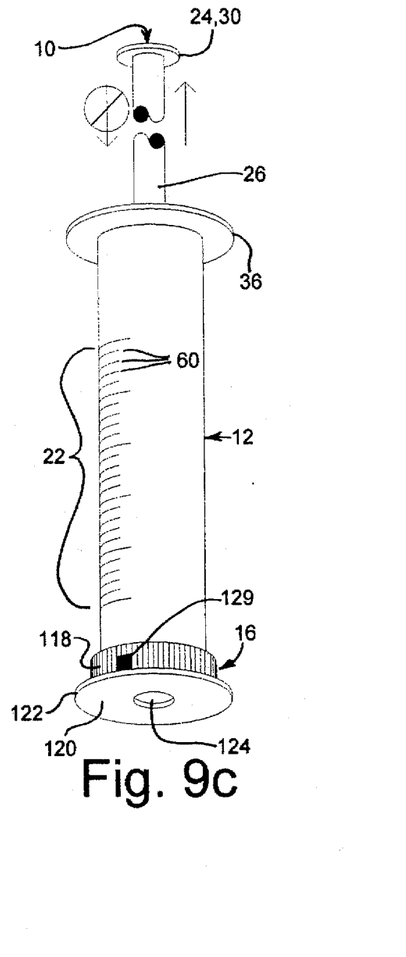
FIG. 9c is an isometric view of the syringe assembly with the needle assembly withdrawn into the syringe body.

As seen in FIG. 8, in a second alternate embodiment of the needle assembly, one of the generally semi-circular plates 108' has a fluid passage 144 located therein. The fluid passage 144 of the generally semi-circular plate 108 is either aligned (view window over first yellow portion) or mis-aligned (view window over green portion 46, second yellow portion 50 or red portion 52), with the top portion 104 and the bottom portion 102 of the cylindrical middle section 66. When the fluid passage 144 of the plate 108 is aligned with the top portion 104 and the bottom portion 102 fluid connection is enabled between the fluid reservoir 22 and the needle 72, otherwise fluid connection is disabled.

Figures 10A, 10B:
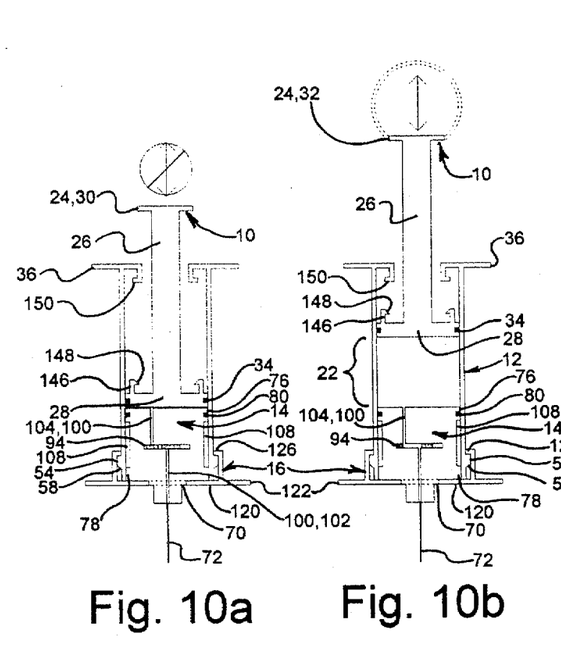
FIG. 10a is a cutaway syringe body and needle assembly view of the syringe assembly in a new state.
FIG. 10b is a cutaway syringe body and needle assembly view of the syringe assembly in use.
Figure 10C:
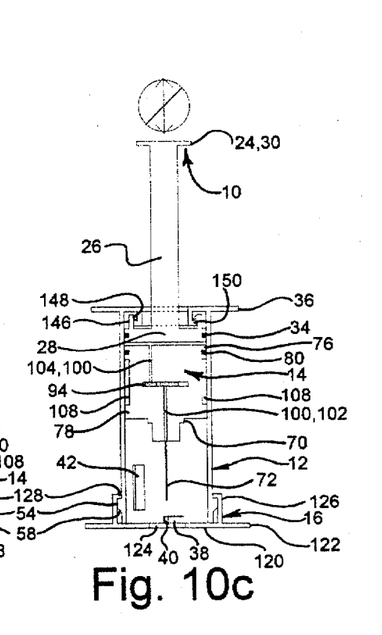
FIG. 10c is a cutaway syringe body and needle assembly view of the syringe assembly with the needle assembly withdrawn into the syringe body.
Figures 11A, 11B:
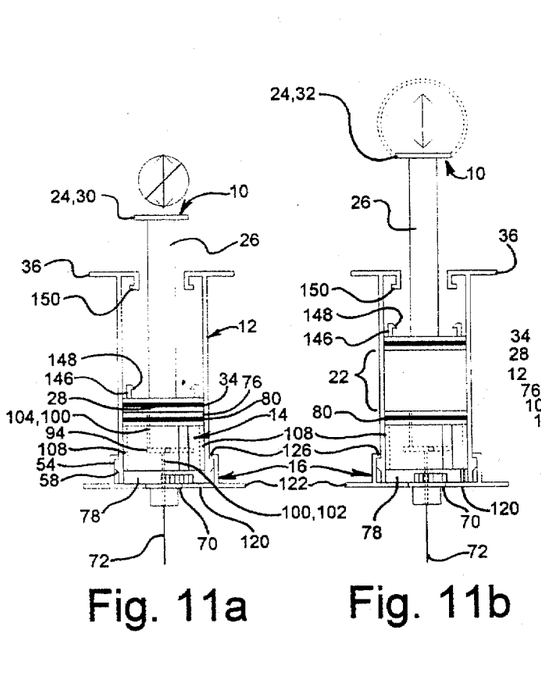
FIG. 11a is a cutaway syringe body view of the needle assembly in a new state.
FIG. 11b is a cutaway syringe body view of the needle assembly in use.
Figure 11C:
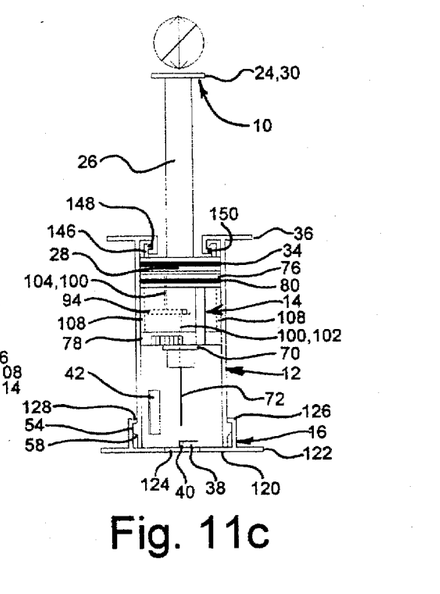
FIG. 11c is a cutaway syringe body view of the needle assembly withdrawn into the syringe body.

As seen in FIGS. 10 and 11, the plunger 10 can be permanently locked into an extended position. As seen, the base 28 of the plunger 10 has one or more inwardly facing springed hooks 146. The end of each hook 146 have a ramped portion 148. When the plunger 10 is pulled near the end of its slide path, the ramped portion 148 passes over a hooked lip 150 of the syringe body 12. Once the ramped portion 148 clears the hooked lip 150, the hooked end clicks into place with the hook 146 grasping the hooked lip 150 and thereby prevents retreat of the plunger 10.

Figure 12:
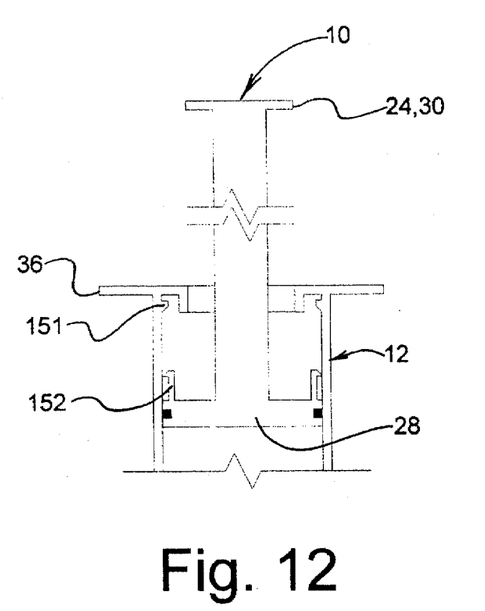
FIG. 12 is a cutaway syringe body and plunger view of the first plunger retention means.

As seen in FIG. 12 an alternate embodiment of the plunger assembly, the plunger 10 has a one or more hooks 146 each with an outwardly extending hooked end 152, located on the plunger base 28. When the plunger 10 is pulled near the end of its slide path, the hooked ends 152 pass over a hooked lip 151 of the syringe body 12. Once the hooked ends 152 clears the hooked lip 150, the hooked end clicks into place with the hooked end 152 grasping the hooked lip 150 and thereby prevents retreat of the plunger 10.

Figure 13:
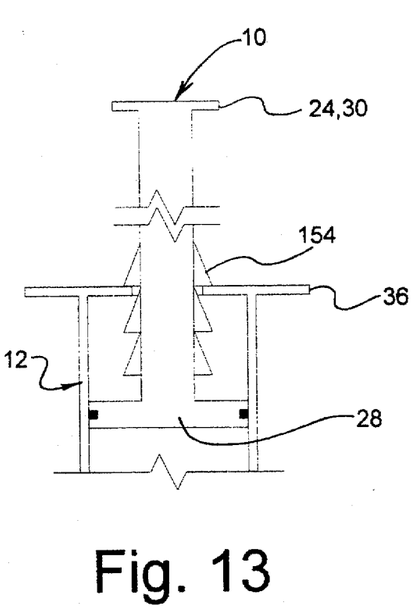
FIG. 13 is a cutaway syringe body and plunger view of the second plunger retention means.

As seen in FIG. 13 a second alternate embodiment of the plunger assembly the plunger 10 has a plurality of one way ramps 154 located on its shaft 26. When the plunger 10 is pulled near the end of its slide path, the one way ramps 154 pass over the end of the syringe body 12. Once the one way ramps 154 clear the end of the syringe body 12, the base of the one way ramp 154 prevents retreat of the plunger.

While the invention has been particularly shown and described with reference to an embodiment thereof, it will be understood by those skilled in the art that various changes in form and detail may be made without departing from the spirit and scope of the invention.

I claim:

1. A retractable syringe comprising:
  a) a hollow syringe body, having a plunger end, a needle end, and a fluid reservoir located therebetween;
  b) a plunger assembly, having a shaft, a base located on one end of the shaft, and a handle located on the opposing end of the shaft, slidably disposed within the syringe body at the plunger end;
  c) a needle in fluid connection with the fluid reservoir;
  d) a fluid connection means, disposed within the syringe body at the needle end, for selectably enabling and disabling fluid connection between the needle and the fluid reservoir;
  e) a rotation means, engaging the fluid connection means, for facilitating rotation of the fluid connection means; and
  f) a retraction means, hydrostatically engaging the fluid connection means with the plunger, for facilitating retraction of the fluid connection means and the needle into the syringe body.

2. The device as in claim 1 wherein the fluid connection means comprises:
  a) a cylindrical body, having a top section having a first encompassing flange portion, a bottom section having a second encompassing flange portion and having the needle attached to the base of the bottom, and a cylindrical middle section slidably and rotatably disposed within the syringe body opposite the plunger end with the top section facing the plunger end;
  b) one or two spaced apart slotted portions located on the second flange;
  c) one or two spaced apart rectangular protrusions, in corresponding number to the number of slotted portions, located within the syringe body;
  d) a horizontally disposed slot passing through the cylindrical middle section;
  e) a first fluid passage extending from the top portion to the horizontally disposed slot laterally offset from the central axis of the cylindrical body;
  f) a second fluid passage extending from the horizontally disposed slot to the needle;
  g) one or two generally semi-circular plates, placed around the middle section;
  h) one or two spaced apart protrusion slots, in corresponding number to the number of rectangular protrusions, for receiving the rectangular protrusions;
  i) a disc, having a disc aperture, first end received within one of the plates, and a second end received within the same one of the plates or the other one of the plates, slidably disposed within the horizontally disposed slotted portion; and
  wherein when the disc aperture is aligned with the first fluid passage and the second fluid passage the fluid reservoir is in fluid connection with the needle and wherein when the disc aperture is mis-aligned with the first fluid passage and the second fluid passage the fluid reservoir is not in fluid connection with the needle.

3. The device as in claim 2 wherein the rotation means comprises:
  a) an open ended tube having a base and a knurled outer circumference;
  b) a non-symmetric-shaped base protrusion located on the bottom section of the needle assembly; and
  c) an aperture, in corresponding shape to the shape of the base protrusion, located in the base of the rotation means which receives and engages the base protrusion.

4. The device as in claim 3 further comprising:
  a) one or more sets of color bands, located on the syringe tube, with each of the one or more sets having a plurality of different color portions; and
  b) one or more view windows, in corresponding number to the number of sets of color bands, located on the knurled tube such that each of the one or more windows aligns with one of the color portions.

5. The device as in claim 4 further comprising a lock means for selectably locking, either temporarily or permanently, the disc aperture into mis-aligned state with the first fluid passage and the second fluid passage.

6. The device as in claim 5 wherein the lock means comprises;
  a) one or more syringe tabs located on the inner circumference of the syringe body;
  b) one or more notch sets, in corresponding number to the number of syringe tabs, located on the second flange of the needle assembly, with each notch set receiving a corresponding tab and having a first notch, a second notch, a third notch, and a fourth notch; and
  c) one or more ramp sets, in corresponding number to the number of notch sets, located on the second flange with each ramp set having a first one-way ramp disposed between the first notch and the second notch, a two-way ramp disposed between the second notch and the third notch, and a second one-way ramp disposed between the third notch and the fourth notch.

7. The device as in claim 1 wherein the fluid connection means comprises:
  a) a cylindrical body, having a top section having a first encompassing flange portion, a bottom section having a second encompassing flange portion and having the needle attached to the base of the bottom, and a cylindrical middle section slidably and rotatably disposed within the syringe body opposite the plunger end with the top section facing the plunger end;
  b) one or two spaced apart slotted portions located on the second flange;
  c) one or two spaced apart rectangular protrusions, in corresponding number to the number of slotted portions, located within the syringe body;
  d) a slot, having a round section, a vertical section, and horizontal section integrally disposed therebetween, passing through the cylindrical middle section;
  e) a first fluid passage extending from the top portion to the round section;
  f) a second fluid passage extending from the round section to the needle;
  g) a first generally semi-circular plate, having a diagonally disposed slotted portion, placed around the middle section;
  h) a second generally semi-circular plate placed around the middle section;
  i) one or two spaced apart protrusion slots, in corresponding number to the number of rectangular protrusions, located within the encompassing second flange, for receiving the rectangular protrusions;

j) a tumbler, having a tumbler aperture and an extension received within the diagonally disposed slotted portion, rotatably disposed within the round section; and wherein when the tumbler aperture is aligned with the first fluid passage and the second fluid passage the fluid reservoir is in fluid connection with the needle and wherein when the tumbler aperture is mis-aligned with the first fluid passage and the second fluid passage the fluid reservoir is not in fluid connection with the needle.

8. The device as in claim 7 wherein the rotation means comprises:

a) an open ended tube having a base and a knurled outer circumference;

b) a non-symmetric-shaped base protrusion located on the bottom section of the needle assembly; and     c) an aperture, in corresponding shape to the shape of the base protrusion, located in the base of the rotation means which receives and engages the base protrusion.

9. The device as in claim 8 further comprising:

a) one or more sets of color bands, located on the syringe body, with each of the one or more sets having a plurality of different color portions; and     b) one or more view windows, in corresponding number to the number of sets of color bands, located on the knurled tube such that each of the one or more windows aligns with one of the color portions.

10. The device as in claim 9 further comprising a lock means for selectably locking, either temporarily or permanently, the disc into mis-aligned state with the first fluid passage and the second fluid passage.

11. The device as in claim 10 wherein the lock means comprises;

a) one or more syringe tabs located on the inner circumference of the syringe body;

b) one or more notch sets, in corresponding number to the number of syringe tabs, located on the second flange of the needle assembly, with each notch set receiving a corresponding tab and having a first notch, a second notch, a third notch, and a fourth notch; and     c) one or more ramp sets, in corresponding number to the number of notch sets, located on the second flange with each ramp set having a first one-way ramp disposed between the first notch and the second notch, a two-way ramp disposed between the second notch and the third notch, and a second one-way ramp disposed between the third notch and the fourth notch.

12. The device as in claim 1 wherein the fluid connection means comprises:

a) a cylindrical body, having a top section having a first encompassing flange portion, a bottom section having a second encompassing flange portion and having the needle attached to the base of the bottom, and a cylindrical middle section slidably and rotatably disposed within the syringe body opposite the plunger end with the top section facing the plunger end;

b) one or two spaced apart slotted portions located on the second flange;

c) one or two spaced apart rectangular protrusions, in corresponding number to the number of slotted portions, located within the syringe body;

d) a first fluid passage, laterally offset from the central axis of the cylindrical body, extending from the top portion to the outer surface of the round section;

e) a second fluid passage extending from the surface of the round section to the needle;

f) a first generally semi-circular plate, having a third fluid passage;

h) a second generally semi-circular plate placed around the middle section;

i) one or two spaced apart protrusion slots, in corresponding number to the number of rectangular protrusions, for receiving the rectangular protrusions.

13. The device as in claim 12 wherein the rotation means comprises:

a) an open ended tube having a base and a knurled outer circumference;

b) a non-symmetric-shaped base protrusion located on the bottom section of the needle assembly; and     c) an aperture, in corresponding shape to the shape of the base protrusion, located in the base of the rotation means which receives and engages the base protrusion.

14. The device as in claim 13 further comprising:

a) one or more sets of color bands, located on the syringe body, with each of the one or more sets having a plurality of different color portions; and     b) one or more view windows, in corresponding number to the number of sets of color bands, located on the knurled tube such that each of the one or more windows aligns with one of the color portions.

15. The device as in claim 14 further comprising a lock means for selectably locking, either temporarily or permanently, the disc into mis-aligned state with the first fluid passage and the second fluid passage.

16. The device as in claim 15 wherein the lock means comprises;

a) one or more syringe tabs located on the inner circumference of the syringe body;

b) one or more notch sets, in corresponding number to the number of syringe tabs, located on the second flange of the needle assembly with each notch set receiving a corresponding tab and having a first notch, a second notch, a third notch, and a fourth notch; and     c) one or more ramp sets, in corresponding number to the number of notch sets, located on the second flange with each ramp set having a first one-way ramp disposed between the first notch and the second notch, a two-way ramp disposed between the second notch and the third notch, and a second one-way ramp disposed between the third notch and the fourth notch.

17. The device as in claim 1 further comprising a plunger lock means for permanently disabling the slidability of the plunger when the plunger is fully retracted.

18. The device as in claim 17 wherein the plunger lock comprises:

a) one or more inwardly facing springed hooks, having a ramped hook end, located on the base; and     b) a hooked lip, located on the plunger end of the syringe tube, for receiving the ramped hook end.

19. The device as in claim 17 wherein the plunger lock comprises:

a) one or more outwardly facing springed hooked portions located on the base; and     b) a hooked lip, located on the plunger end of the syringe tube, for receiving the ramped hook end.

20. The device as in claim 17 wherein the plunger lock comprises one or more one way ramps located on the shaft.

* * * * *